United States Patent [19]

Aune

[11] Patent Number: 5,478,848
[45] Date of Patent: Dec. 26, 1995

[54] INHIBITION OF ARTHRITIS BY L-TYPE CALCIUM CHANNEL ANTAGONISTS NIMODIPINE, NISOLDIPINE AND NIFEDIPINE

[75] Inventor: Thomas M. Aune, Hamden, Conn.

[73] Assignee: Bayer Corporation, Pittsburgh, Pa.

[21] Appl. No.: 188,464

[22] Filed: Jan. 26, 1994

[51] Int. Cl.$^6$ ..................................................... A61K 31/44
[52] U.S. Cl. ........................................... 514/356; 514/355
[58] Field of Search ..................................... 514/355, 356

[56] References Cited

U.S. PATENT DOCUMENTS

| | | | |
|---|---|---|---|
| Re. 33,963 | 6/1992 | Hegasy | 424/78.24 |
| 3,932,645 | 1/1976 | Meyer et al. | 424/266 |
| 4,154,839 | 5/1979 | Wehinger et al. | 424/266 |
| 4,537,898 | 8/1985 | Hoff et al. | 514/356 |
| 4,600,778 | 7/1986 | Teller et al. | 546/249 |
| 4,783,337 | 11/1988 | Wong et al. | 424/468 |
| 4,788,205 | 11/1988 | Cooper et al. | 514/333 |
| 4,857,312 | 8/1989 | Hegasy et al. | 514/344 |
| 4,892,730 | 1/1990 | Hegasy | 424/80 |
| 4,892,741 | 1/1990 | Ohm et al. | 424/479 |
| 4,981,683 | 1/1991 | Hegasy et al. | 424/80 |
| 4,988,717 | 1/1991 | Wehinger et al. | 514/356 |

OTHER PUBLICATIONS

Gay and Gay, *Rheumatol. Int.* 9, 105–113 (1989).
Kouri et al., *Scand. J. Immunol.* 19, 359–364 (1984).
Burmester et al., *Scand. J. Immunol.* 17, 68–82 (1983).
Baumgarten and Villereal, *J. Biol. Chem.* 267, 1524–10530 (1992).
Bernini et al., *J. Cardiovasc. Pharmacol.* 18, 42–45 (1991).
Hijioka et al., *Mol. Pharmacol.*, 4, 435–440 (1992).
Kong et al., *Second Messenger Phosphoproteins* 13, 117–130 (1991).
Olsen et al., *Biochem. Biophys. Res. Commun.* 162, 448–455 (1989).
Dayer and Demczuk, *Cytokines and Other Mediators in Rheumatoid Arthritis*, Springer Seminars in Immunopathology, pp. 1–27 (Springer–Verlag 1984).
Gay and Koopman, *Current Opinion in Rheumatology* 1, 8–14 (1989).
Brennan et al., *The Lancet* Jul. 29, 224–247 (1989).
Taurog et al., *Meth. Enzymol.* 162, 339–355 (1988).
Otterness and Bliven et al., *Nonsteroidal Anti–Inflammatory Drugs*, pp. 111–252 (1985).
Ward, *Am. J. Med.*, pp. 3–9 (1984).
Triggle and Janis, *Structure and Physiology if the Slow Inward Calcium Channel*, pp. 51–70 (1987).
Godfraind et al., *Pharmacol. Rev.* 38, 321–416 (1986).
Janis and Triggle, *Drug Dev. Res.* 4, 257–274 (1984).
Schramm et al., *Nature* 303, 535–537 (1983).
Scriabine, *Rational Drug Therapy* 21, 1–17 (1987).
Chen et al., *Science* 239, 1024 (1988).
Scriabine, *Structure and Physiology of the Slow Inward Calcium Channel*, pp. 51–70 (1987).
Jeurissen et al., *Arthritis and Rheumatism* 34, 961–972 (1991).
Yocum et al., *Annals of Internal Medicine* 109, 863–869 (1988).
Rau et al., *Arthritis and Rheumatism* 34, 1236–1244 (1991).

*Primary Examiner*—T. J. Criares

[57] ABSTRACT

The present invention comprises new methods for treating rheumatoid arthritis. It has been found that the L-type calcium channel antagonists are effective in treating arthritis. Nimodipine, nisoldipine, and nifedipine, are examples of specific compounds useful in the present invention.

8 Claims, 1 Drawing Sheet

INHIBITION OF ARTHRITIS BY L-TYPE CALCIUM CHANNEL ANTAGONISTS NIMODIPINE, NISOLDIPINE AND NIFEDIPINE

BACKGROUND OF THE INVENTION

1. Field of the Invention

This invention relates to methods of using L-type calcium channel antagonists to treat arthritis.

2. Description of the Prior Art

Rheumatoid arthritis is a debilitating disease of the connective tissue. It most often manifests itself through inflammation and thickening of the synovial membranes, the sacs that hold the fluid (synovial fluid) that lubricates the joints. It generally causes irreversible damage to the joint capsule and the articular cartilage. There is evidence that suggests that an autoimmune mechanism may play a role in the disease.

Synovium is composed of two cell types termed type A synoviocytes and type B synoviocytes. (Gay and Gay, *Rheumatol Int.* 9, 105–113 (1989); Kouri et al., *Scand. J. Immunol* 19, 359–364 (1984); Burmester et al., *Scand. J. Immunol.* 17, 68–82 (1983)). Type A synoviocytes resemble tissue macrophages and type B synoviocytes resemble fibroblasts. Certain examples of tissue macrophage-like cells and fibroblasts possess calcium channels that resemble L-type calcium channels. Baumgarten and Villereal, *J. Biol. Chem.* 267, 10524–10530 (1992); Bernini et al., *J. Cardiovasc. Pharmacol.* 18, 42–45 (1991); Hijioka et al., *Mol. Pharmacol.* 41, 435–440 (1992); Kong et al., *Second Messenger Phosphoproteins* 13, 117–130 (1991); Olsen et at. *Biochem. Biophys. Res. Commun.* 162, 448–455 (1989). The evidence that suggests that certain macrophage- or fibroblast-like cells have L-type calcium channels includes: 1) electrophysiologic studies, 2) inhibition of calcium currents by selective L-type calcium channel antagonists, and 3) activation of calcium currents by selective L-type calcium channel agonists. In rheumatoid arthritis, type A cells and type B cells participate in the inflammatory process.

A hallmark of rheumatoid arthritis is the formation of a "pannus," which results from massive proliferation of synoviocytes. Synoviocytes are known to release inflammatory cytokines and other mediators as well as proteases and other enzymes that contribute to the tissue destruction associated with rheumatoid arthritis. Dayer and Demczuk, *Cytokines and Other Mediators in Rheumatoid Arthritis*, Springer Seminars in Immunopathology. 1–27 (Springer-Verlag 1984); Gay and Koopman, *Current Opinion in Rheumatology* 1, 8–14 (1989); Brennan et al., The Lancet Jul. 29, 224–247 (1989).

Adjuvant-induced arthritis is an experimental disease unique to laboratory rats. It occurs after inoculation with an oily emulsion or suspension of material possessing Freund's type adjuvant activity. Adjuvant-induced arthritis is a widely-used model for studying the physiology, biochemistry, and pharmacology of inflammation as well as a model of cell-mediated autoimmune disease, human arthritis, and chronic pain. Taurog et al., *Meth. Enzymol* 162, 339–355 (1988). As a model system, adjuvant arthritis has predicted clinical potency and efficacy for non-steroidal anti-inflammatory drugs NSAIDs used for rheumatoid arthritis. This is also the case for immunosuppressive agents, such as cyclosporin, and cytotoxic agents such as cyclophosphamide or methotrexate. Except for methotrexate, this latter class of drugs is not widely used for the treatment of rheumatoid arthritis because of problems with toxicity. A certain level of toxicity is also associated with the use of NSAIDs. Otterness and Bliven, *Nonsteroidal Anti-inflammatory Drugs* 111–252 (1985). The most common and perhaps most severe side effect is gastrointestinal bleeding. For example, ulceration of the upper gastrointestinal tract leading to gastrointestinal bleeding is common with therapeutic doses of indomethacin used in the treatment of rheumatoid arthritis. This is also the case for other NSAIDs.

Methotrexate has recently been approved for the treatment of severe, active rheumatoid arthritis. Hepatic fibrosis and cirrhosis have been reported in patients being treated for rheumatoid arthritis with methotrexate, however. There has also been evidence of progressive dose-related hepatic changes during extended periods of treatment that correlates with ethanol ingestion.

Indomethacin was introduced in 1963 to treat rheumatoid arthritis. Although it is widely used because of its efficacy, toxicity often limits its use. From 35 to 50 percent of patients receiving standard therapeutic doses of indomethacin experience untoward side effects, and about 20 percent are forced to discontinue its use.

The drug sulindac was developed in an attempt to find an effective, but less toxic alternative to indomethacin. It is only half as potent as indomethacin, however, and has toxic side effects of its own.

In view of the foregoing, alternative methods for the treatment of rheumatoid arthritis are desirable.

SUMMARY OF THE INVENTION

An object of the present invention is to provide a new and useful method for treating arthritis in mammals that is both safe and effective. The present invention comprises a novel method for the treatment of arthritis in mammals. It has been found that L-type calcium channel antagonists are effective agents for treating arthritis. Dihydropyridnes, phenylalkamines, and benzothiazepines are particular classes of L-type calcium channel antagonists that are useful in the methods of the present invention. Specific compounds that are useful in the invention are the dihydropyridines nimodipine, nisoldipine, and nifedipine as well as the phenyl-alkylamine verapamil and the benzothiazepine diltiazem. Effective dosages range from about 1 mg antagonist/day to about 1 g antagonist/day.

DETAILED DESCRIPTION OF THE INVENTION

Figure 1:
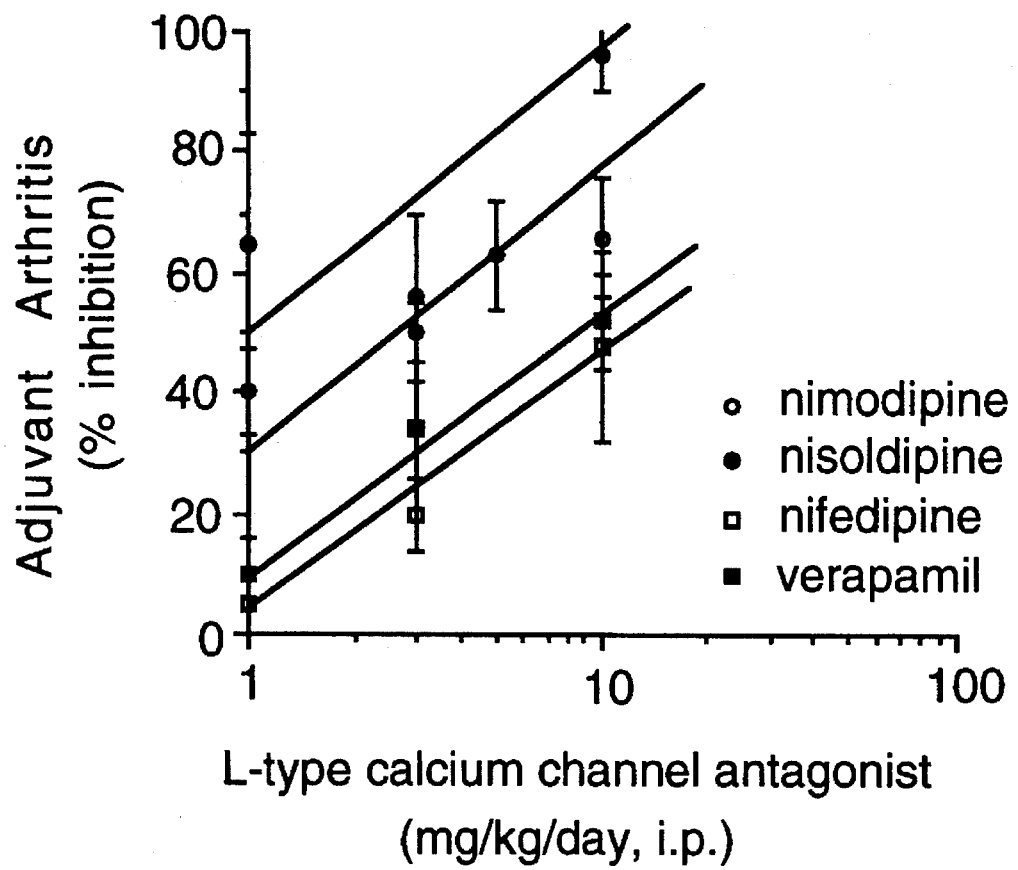
FIG. 1 displays the inhibition of adjuvant-induced arthritis by nimodipine, nisoldipine, nifedipine, and verapamil.

The $Ca^{2+}$ channel antagonists known as the 1,4-dihydropyridines (DHPs) have been shown to be highly potent and specific inhibitors of $Ca^{2+}$ entry into excitable cells through L-type $Ca^{2+}$ channels. Scriabine, *Receptor Biochem. and Method.* 9, 51–70 (1987); Triggle and Janis, *Receptor Biochem. and Method.* 9, 29–50 (1987); Godfraind et al., *Pharmacol. Rev.* 38, 321–416 (1986); Janis and Triggle, *Drug Dev. Res.* 4, 257–274 (1984); Schramm et al., *Nature* 303 535–537 (1983); Scriabine, *Rational Drug Therapy* 21, 1–7 (1987). More recently, a number of investigators have also demonstrated that certain non-excitable cells also contain DHP-sensitive $Ca^{2+}$ channels that appear to be similar to L-type channels. Hijioka et al., supra; Chen et al., *Science*

239, 1024 (1988); Kong et al., supra; Olsen et al., supra; and Baumgarten et al., supra. Concentrations of DHPs known to interfere with the $Ca^{2+}$ movements in excitable cells also interfere with entry of $Ca^{2+}$ ions into certain non-excitable cells. Entry of $Ca^{2+}$ into these cells is also stimulated by $K^+$-induced depolarization and/or by the L-type $Ca^{2+}$ channel agonist Bay K 8644. Examples of such cells include fibroblasts, macrophage/monocyte-like cells, and Kuppfer cells.

As noted previously, evidence suggests that type A and type B synoviocytes may contain L-type $Ca^{2+}$ channels. And because these synovial cells are believed to participate in the inflammatory response in rheumatoid arthritis, I set out to determine whether selective L-type $Ca^{2+}$ channel antagonists would affect these cells and, in turn, reduce the inflammatory response associated with rheumatoid arthritis.

There are several classes of selective L-type calcium channel inhibitors. One class mentioned before, the 1–4-dihydropyridines, has the following general structure:

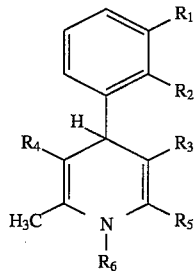

A number of compounds of this type have been shown to have L-type calcium channel inhibition activity. E.g., Scriabine in *Structure and Physiology of the Slow Inward Calcium Channel*, pp. 51–70 (Alan R. Liss, Inc., 1987) and references cited therein. Table 1 presents structures for several of these compounds.

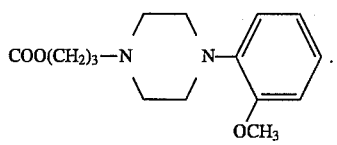

Some of these compounds have fused ring structures. For instance, darodipine has the following structure:

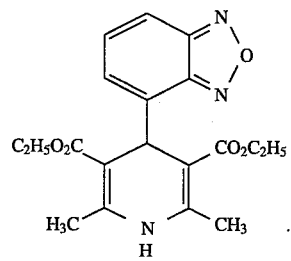

Other 1,4-dihydropyridine L-type calcium channel antagonists include SKF 24260, ryosidine, niludipine, nitrendipine, ryodipine, felodipine, nilvadipine, amlodipine, FR 7534, KW 3049, flordipine, PN 200-110, mesudipine, 8363-s and oxodipine. These compounds are more fully described in Scriabine, id., and references cited therein. Synthesis of some of these 1,4-dihydropyridines and others is described by Wehinger et al., U.S. Pat. Nos. 4,988,717 and 4,154,839, Teller et al., U.S. Pat. No. 4,600,778, and Meyer et al., U.S. Pat. No. 3,932,645, all of which are hereby incorporated by reference.

TABLE 1

|  | Nifedipine | Nisoldipine | Nimodipine |
| --- | --- | --- | --- |
| $R_1$ | H | H | $NO_2$ |
| $R_2$ | $NO_2$ | $NO_2$ | H |
| $R_3$ | —$COCCH_3$ | —$COOCH_3$ | —$COO(CH_2)_2OCH_3$ |
| $R_4$ | —$COCCH_3$ | —$COOCH_2CH(CH_3)_2$ | —$COCCH(CH_3)_2$ |
| $R_5$ | $CH_3$ | $CH_3$ | $CH_3$ |
| $R_6$ | H | H | H |
|  | Nicardipine | Nivaldipine | Amlodipine |
| $R_1$ | $NO_2$ | $NO_2$ | H |
| $R_2$ | H | H | Cl |
| $R_3$ | —$CO_2(CH_2)_2N(CH_3)_2$ | —$COOCH_3$ | —$COOC_2H_5$ |
| $R_4$ | —$COCCH_3$ | —$COOCH(CH_3)_2$ | —$COOCH_3$ |
| $R_5$ | $CH_3$ | $CN$ | —$CH_2O(CH_2)_2NH_2$ |
| $R_6$ | H | H | H |

1,4-dihydropyridine L-type calcium channel antagonists may also have heterocyclic and aromatic moieties. For example, the 1,4-dihydropyridine BM 20064 is the same as nicardipine except that the BM 20064 $R_3$ group is:

The benzothiazepines are another class of L-type calcium channel antagonists. Diltiazem is a benzothiazepine having the following structure:

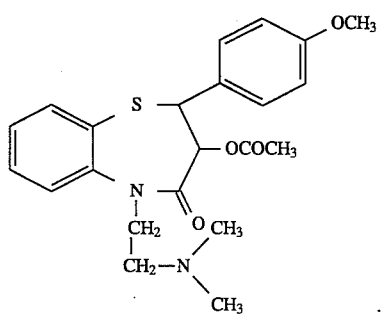

Scriabine, id., and references cited therein provide other examples of benzo-thiazepine L-type calcium channel antagonists, including RT 362 and fostedil.

The phenylalkylamines are still another class of L-type calcium channel antagonist. Verapamil is the best known of these, having the following structure:

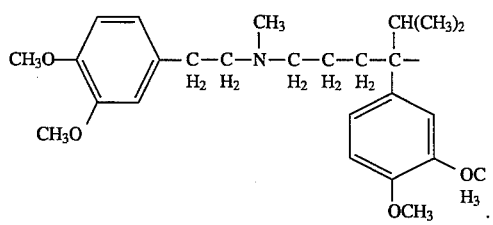

Other phenylalkylamines with calcium channel antagonist activity are prenylamine, gallopamil, fendiline, terodiline, tiapamil, anipamil, ronipamil, HOE 263, and SC-30552. Scriabine, id., and references cited therein provide other examples of phenylalkylamine L-type calcium channel antagonists, All of the aforementioned compounds are known in the art and many are commercially available.

A model for rheumatoid arthritis that was used to demonstrate the efficacy of the compounds of the present invention was adjuvant-induced arthritis in rats. (Otterness and Bliven, supra.) Although it does not share all features with rheumatoid arthritis in humans, it does bear a number of significant similarities. One similarity is the sensitivity to certain therapeutic treatments known to be active in humans. Also, therapeutic doses in humans are similar to therapeutic doses in the adjuvant arthritis model. Examples include NSAIDs, steroids, methotrexate, immunosuppressive drugs, such as cyclosporin, and cytotoxic drugs, such as cyclophosphamide and allopurinol. Jeurissen et. al., *Arthritis and Rheumatism* 34, 961–972 (1991); Yocum et. al., *Annals of Internal Medicine* 109, 863–869 (1988); Rau, et. al., *Arthritis and Rheumatism* 34, 1236–1244 (1991); Otterness and Bliven, supra; Ward, *Am. J. Med. Medicine*. pp. 3–9 (Jul. 13, 1984).

Another arthritis model often used is the passive transfer model. In the passive transfer model of adjuvant arthritis, spleen cells are harvested from animals 12–14 days after the animals have been injected with adjuvant, cultured 24 hours in vitro with the T-cell mitogen, concanavaLin A, and injected into naive rats. Within 14–20 days, arthritis develops in the paws. Transfer of naive spleen cells, or spleen cells from animals immunized with an irrelevant antigen, does not result in the development of arthritis. Published data indicate that sensitized T-cells transfer disease. Otterness and Bliven, supra.

The development of adjuvant-induced arthritis is believed to be separable into four distinct components. The first corresponds to sensitization (days 0–4), the second corresponds to the production of immunocompetent cells (days 6–10), the third corresponds to the development of hypersensitivity reactions (days 11–14) and the fourth corresponds to the development of established disease (days 14–18). In the passive transfer model, immunocompetent cells are transferred directly into animals. This may be more representative of treatment of rheumatoid arthritis since these individuals also already have immunocompetent T cells.

I have found that L-type calcium channel antagonists are effective in the treatment of arthritis. In a preferred embodiment of the invention, a therapeutically effective amount of an L-type calcium channel antagonist is administered to a mammal. In another preferred embodiment, one or more compounds chosen from the group consisting of the dihydropyridines, the phenyl-alkylamines, the benzothiazepines and mixtures thereof is administered in therapeutically effective amounts. In another preferred embodiment of the invention, the dihydropyridines are chosen from the group consisting of nisoldipine, nimodipine, and nifedipine, the phenylalkylamine verapamil, and the benzothiazepine diltiazem, each of which is effective in the treatment of arthritis. In another preferred embodiment of the present invention, nisoldipine, nimodipine, nifedipine, verapamil, diltiazem or mixtures thereof is administered in an amount in the range from about 1 mg antagonist/day to about 1 g antagonist/day.

It will be understood, however, that the specific dose level for any particular patient will depend upon a variety of factors, including the activity of the specific compound employed, the age, body weight, general health, sex, diet, time of administration, route of administration, and rate of excretion, drug combination and the severity of the disease undergoing therapy.

The L-type calcium channel antagonists may be administered orally, topically, parenterally, by inhalation or spray or rectally in dosage unit formulations containing conventional non-toxic pharmaceutically acceptable carriers, adjuvants and vehicles. Spray formulations of dihydropyridines are described by Hegasy et al. in U.S. Pat. No. 4,857,312, which is hereby incorporated by reference. The term parenteral as used herein includes subcutaneous injections, intravenous, intramuscular, intrasternal injection or infusion techniques. In addition, there is provided a pharmaceutical formulation comprising an L-type calcium channel antagonist and a pharmaceutically acceptable carrier. One or more L-type calcium channel antagonists may be present in association with one or more non-toxic pharmaceutically acceptable carriers and/or diluents and/or adjuvants and if desired other active ingredients. The pharmaceutical compositions containing L-type calcium channel antagonists may be in a form suitable for oral use, for example, as tablets, troches, lozenges, aqueous or oily suspensions, dispersible powders or granules, emulsion, hard or soft capsules, or syrups or elixirs.

The preferred method of administration is oral. Compositions intended for oral use may be prepared according to any suitable method known to the art for the manufacture of pharmaceutical compositions. Such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Dihydropyridines may be prepared in solid, rapidly released form, as taught by Hegasy, U.S. Pat. Nos. 4,981,683, 4,892,730, and U.S. Pat. No. Re. 33,963, which are hereby incorporated by reference. Ohm et al., U.S. Pat. No. 4,892,741, which is hereby incorporated by reference, describes a process for preparing solid pharmaceutical preparations of dihydropyridines in the form of press coated tablets.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil. In the preferred embodiment, the L-type calcium channel inhibitors are administered orally in the form of a soft gelatin capsule.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Dihydropyridines may also be in the form of non-aqueous liquid formulations, as taught by Hoff et al., U.S. Pat. No. 4,537,898, which is hereby incorporated by reference.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or di- glycerides. In addition, fatty acids such as oleic acid find use in the preparation of injectables.

The L-type calcium channel antagonists may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

L-type calcium channel antagonists may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

It will be appreciated by those skilled in the art that the particular method of administration will depend on a variety of factors, all of which are considered routinely when administering therapeutics. It will also be appreciated that any therapeutically active form of the L-type calcium channel inhibitor is suitable for use in the present invention.

Extensive information concerning the toxicity of nimodipine and nisoldipine is available. (NDA application to the FDA for nisoldipine, Miles, Inc.; NDA application to the FDA for nimodipine, Miles, Inc.) Studies on the toxicity profile of nimodipine and nisoldipine, even at supra-therapeutic concentrations, have not revealed any gastrointestinal irritation. This is demonstrated by macroscopic and microscopic (histological) analysis of the gastrointestinal tract as well as analysis of the presence of fecal blood after acute, sub-acute, and chronic exposure to nimodipine and nisoldipine. At the expected therapeutic dose for nisoldipine and nimodipine in rheumatoid arthritis, no gastrointestinal toxicity has been observed, even after prolonged periods of treatment. Thus, nisoldipine, nimodipine, and other L-type calcium channel antagonists have certain advantages over NSAIDS and other traditional drugs used for treatment of rheumatoid arthritis.

The following examples are intended to illustrate the efficacy of the present invention and not to limit its scope in any way.

EXAMPLES

In each of the following Examples, the DHPs, nimodipine, nisoldipine and nifedipine were obtained from Miles, Inc., West Haven, Conn. 06516. Adjuvant was from Difco. Verapamil was obtained from Research Biochemicals, Inc., Natick, Mass. 01760. Diltiazem may be obtained, for example, from SIGMA® Chemical Co. (St. Louis, Mo.).

Example 1

Inhibition of arthritis in the adjuvant-induced arthritis model

Lewis rats were given a 0.1 ml injection of adjuvant (1 mg/animal) into the base of the tail on day 0. Swelling of the feet and ankles was first noted on days 10– 12. Maximal swelling was observed on days 16–20. The cell infiltrate of the chronic inflammatory responses is predominantly mononuclear (indicating the presence of cell-mediated immunity). Animals were observed daily, and ankle diameter was measured in millimeters on days 12 and 16 using a hand-held dial micrometer. The degree of swelling was assessed by calculating the mean difference between day 16 and day 0 ankle diameter. The results are expressed as the percent inhibition of the increase in ankle diameter on day 16. At this point the animals were sacrificed and tissues were taken for histologic evaluation.

Animals were administered test drugs, suspended in 5% polyethylene glycol and 0.5% Tween-80 in phosphate buffered saline (p.o. or i.p.) once each day from day 1 to day 16.

FIG. 1 presents the results for a range of dosages. Inhibition of swelling was observed at doses between 1 and 10 mg antagonist/kg body weight/day of all L-type calcium channel antagonists tested.

Table 1 compares the efficacy of L-type calcium channel antagonists with that of indomethacin. The results are expressed as $ED_{50}$ in mg antagonist/kg body weight/day for i.p. dosage. The results show that the most active L-type calcium channel antagonists, nisoldipine and nimodipine, are comparable in potency to indomethacin. The rank order of potency of the dihydropyridines was identical to their potency as $Ca^{2+}$ channel antagonists. (Yousif and Triggle, Can. J. Physiol. Pharmacol. 64, 273–283 (1986)).

TABLE 1

Comparison of the potency of different L-type calcium channel antagonists with indomethacin in the adjuvant arthritis model in the Lewis rat.

| Drug | $ED_{50}$ (mg antagonist/kg body weight/day) |
| --- | --- |
| nisoldipine | <1 |
| nimodipine | 4 |
| nifedipine | 11 |
| verapamil | 10 |
| indomethacin | 3 ± 1 |

Histologic analysis of tissues from arthritic animals treated with the dihydropyridine L-type calcium channel antagonists shows inhibition of (a) erosion of bone and cartilage, (b) infiltration of neutrophils, and (c) thickening of the synovial lining.

Example 2

Inhibition of adjuvant-induced arthritis with the benzothiazepine L-type calcium channel inhibitors The same protocol described in Example 1 is followed for determining the affect of the benzothiazepine L-type calcium channel antagonist diltiazem on adjuvant-induced arthritis in rats. It is found that diltiazem is effective at inhibiting adjuvant-induced arthritis when administered in dosages in the range of about 1 mg/kg body weight/day to about 20 mg/kg body weight/day.

Example 3

Inhibition of arthritis in the passive transfer model

Arthritis is also induced in the Lewis rat by the passive transfer of spleen cells from a sensitized donor. Nimodipine was also tested for its ability to inhibit arthritis in the passive-transfer model. Otterness and Bliven, supra. Table 2 presents the results. At 10 mg antagonist/kg body weight/day (j.p.) nimodi-pine completely inhibited arthritis in this model.

Spleens were harvested from naive rats or from rats 9–12 days after sensitization with complete Freund's adjuvant. Single cell suspensions from spleen were prepared and cells were cultured for 24 hours with the T cell mitogen, concanavalin A. Spleen cells were harvested and injected, i.v., into naive animals. Ankle diameters were determined 14–18 days after injection of spleen cells from naive or sensitized animals into naive animals. Animals were administered nimodipine at 10 mg/kg/day, i.p., suspended in 5% polyethylene glycol and 0.5% Tween-80 in phosphate-buffered saline.

TABLE 2

Inhibition of the passive transfer of arthritis by nimodipine

| Source of T Cells | Nimodipine (mg/kg/day, i.p.) | Increase in paw diameter (mm) |
| --- | --- | --- |
| Naive | — | 0.0 |
| Sensitized | — | 2.9 ± 0.3 |
| Sensitized | 10 | 0.2 ± 0.05 |

What is claimed is:

1. A method of treating rheumatoid arthritis in mammals comprising administering a therapeutically effective amount of a dihydropyridine L-type calcium channel antagonist selected from the group consisting of nimodipine, nisoldipine, nifedipine, and mixtures thereof.

2. The method of claim 1 wherein the L-type calcium channel antagonist is nimodipine.

3. The method of claim 1 wherein the L-type calcium channel antagonist is nisoldipine.

4. The method of claim 1 wherein the L-type calcium channel antagonist is nifedipine.

5. The method of claim 1 wherein the amount of nimodipine, nifedipine, nisoldipine, and mixtures thereof is in the range of about 1 mg antagonist/kg body weight/day to about 1 g antagonist/day.

6. The method of claim 2 wherein the amount of nimodipine is in the range of about 1 mg antagonist/day to about 1 g antagonist/day.

7. The method of claim 3 wherein the amount of nisoldipine is in the range of about 1 mg antagonist/day to about 1 g antagonist/day.

8. The method of claim 4 wherein the amount of nifedipine is in the range of about 1 mg antagonist/day to about 1 g antagonist/day.

* * * * *